(12) United States Patent
Tekulve et al.

(10) Patent No.: US 9,724,104 B2
(45) Date of Patent: Aug. 8, 2017

(54) ANEURYSM CLOSURE CLIP

(75) Inventors: Kurt J. Tekulve, Ellettsville, IN (US);
Elizabeth A. Theobald, Bloomington, IN (US); Steve Harris, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 402 days.

(21) Appl. No.: 14/241,921

(22) PCT Filed: Aug. 30, 2012

(86) PCT No.: PCT/US2012/053059
§ 371 (c)(1),
(2), (4) Date: Feb. 28, 2014

(87) PCT Pub. No.: WO2013/033341
PCT Pub. Date: Mar. 7, 2013

(65) Prior Publication Data
US 2014/0207155 A1 Jul. 24, 2014

Related U.S. Application Data

(60) Provisional application No. 61/529,959, filed on Sep. 1, 2011.

(51) Int. Cl.
*A61B 17/12* (2006.01)
*A61B 17/128* (2006.01)
(Continued)

(52) U.S. Cl.
CPC .......... *A61B 17/128* (2013.01); *A61B 17/122* (2013.01); *A61B 17/12022* (2013.01);
(Continued)

(58) Field of Classification Search
CPC ........ A61B 17/12022; A61B 17/12113; A61B 17/1245; A61B 17/1215; A61B 17/122;
(Continued)

(56) References Cited

U.S. PATENT DOCUMENTS 4,902,508 A 2/1990 Badylak et al.
5,554,389 A 9/1996 Badylak et al.
(Continued)

FOREIGN PATENT DOCUMENTS

WO WO 2004/019790 A1 3/2004

OTHER PUBLICATIONS

Final Decision for Rejection for Patent Application No. JP 2014-528586, dated Nov. 10, 2015 (with Translation).

*Primary Examiner* — Julie A Szpira
(74) *Attorney, Agent, or Firm* — Brinks Gilson & Lione

(57) ABSTRACT

An aneurysm closure clip along with a system and method for use by a physician in delivering the closure clip into the vasculature of a patient is disclosed. The closure clip delivery system comprises a delivery tube in the form of a catheter, a guide wire, and a detachable closure clip. The closure clip includes a proximal side and a distal side. The distal side comprises at least two winged elements that interact with the wall of the body vessel to hold the clip in place after delivery. The proximal side includes a seal element and a guide bar. The guide bar is in communication with the guide wire during delivery. The seal element forms a barrier between the aneurysm and the rest of the body vessel, thereby, reducing any pressure exerted on the aneurysm. The seal element and optionally the winged elements include a material layer comprised of bioremodelable material, such as an extracellular matrix material (ECM).

15 Claims, 5 Drawing Sheets

(51) Int. Cl.
*A61B 17/122* (2006.01)
*A61B 17/00* (2006.01)

(52) U.S. Cl.
CPC ..... *A61B 17/12113* (2013.01); *A61B 17/1215* (2013.01); *A61B 17/12145* (2013.01); *A61B 2017/00584* (2013.01); *A61B 2017/00606* (2013.01); *A61B 2017/00615* (2013.01); *A61B 2017/12054* (2013.01)

(58) Field of Classification Search
CPC ........ A61B 17/128; A61B 2017/00584; A61B 2017/00606; A61B 2017/00615; A61B 2017/12054
See application file for complete search history.

(56) References Cited

U.S. PATENT DOCUMENTS

| | | | |
|---|---|---|---|
| 5,993,844 | A | 11/1999 | Abraham et al. |
| 6,099,567 | A | 8/2000 | Badylak et al. |
| 6,206,931 | B1 | 3/2001 | Cook et al. |
| 6,508,833 | B2 | 1/2003 | Pavcnik et al. |
| 6,936,055 | B1 | 8/2005 | Ken et al. |
| 2003/0093108 | A1 | 5/2003 | Avellanet et al. |
| 2007/0191884 | A1* | 8/2007 | Eskridge .......... A61B 17/12022 606/213 |
| 2010/0312272 | A1* | 12/2010 | Pavcnik ............. A61B 17/0057 606/213 |

* cited by examiner

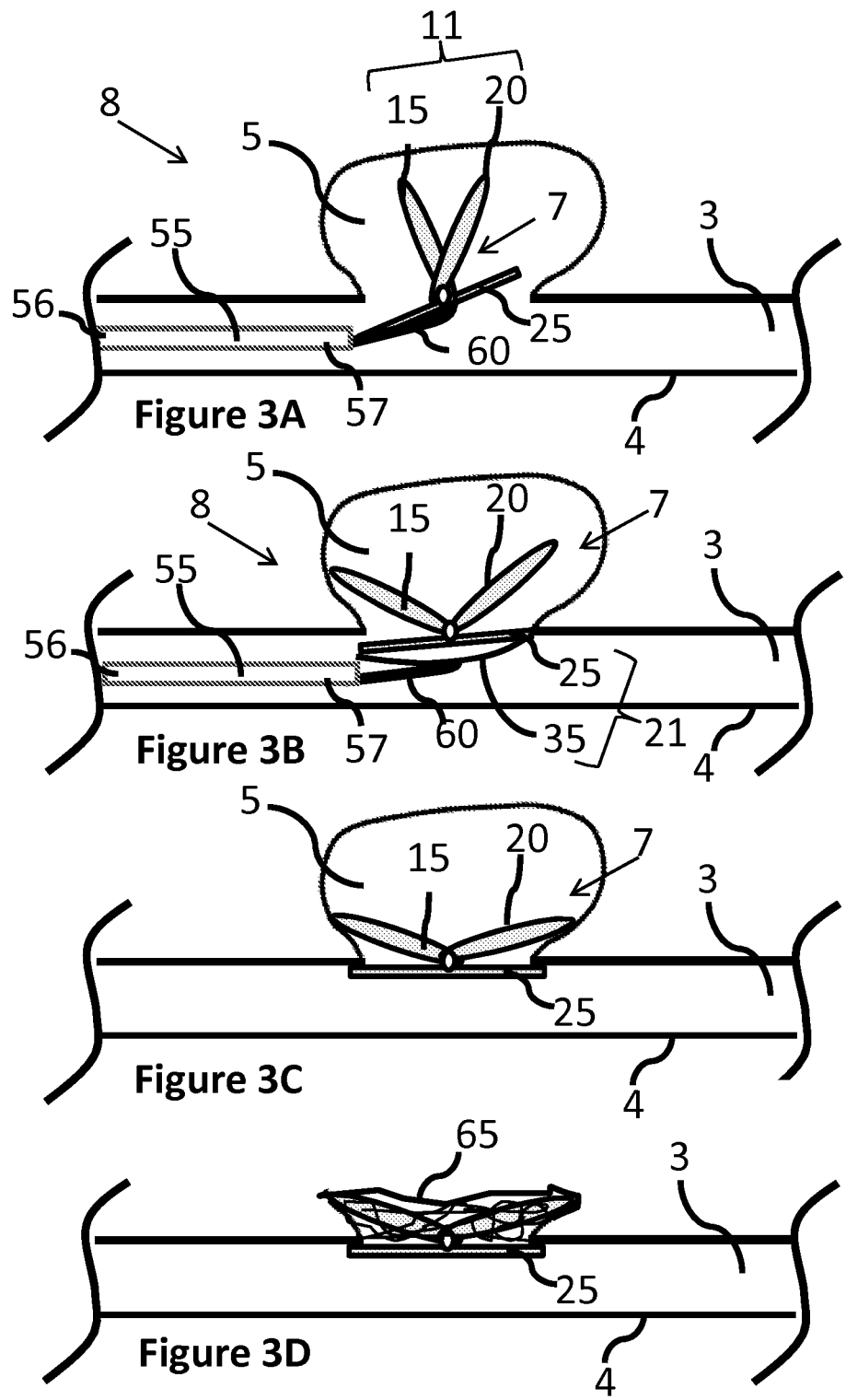

ANEURYSM CLOSURE CLIP

CROSS-REFERENCE TO RELATED APPLICATIONS

This application claims the benefit of U.S. Provisional Application No. 61/529,959, filed on Sep. 1, 2011, entitled "ANEURYSM CLOSURE CLIP," the entire contents of which are incorporated herein by reference.

FIELD

This invention relates generally to the field of methods and devices used for the embolization of vascular abnormalities. More specifically, this invention pertains to a closure clip used in the treatment of an aneurysm.

BACKGROUND

An abnormal bulge or aneurysm may occur in a body vessel due to the weakening of the vessel's wall. If the aneurysm grows large enough it may rupture and produce internal hemorrhaging, which can lead to a life threatening condition. In order to prevent rupturing, physicians have developed various methods, such as surgical clipping, and endovascular treatment. Endovascular treatment includes the use of a balloon or coil to occlude the flow of blood into the vascular abnormality by creating a physical barrier. The selection of either surgery or endovascular treatment depends upon individualized risk factors, the location of the aneurysm, the size of the aneurysm, and the likelihood of complete occlusion.

During endovascular treatment an embolization coil is typically delivered to the location of an aneurysm present in the body vessel or vasculature of a patient through the use of a catheterization procedure. In this procedure, a catheter is inserted into the body vessel and positioned to be proximal to the aneurysm. Then a coil is loaded into the lumen of the catheter and advanced through the catheter until it reaches and exits through the distal end of the catheter. The goal of this treatment is to reduce pressure on the vessel walls at the location of the aneurysm in order to prevent the aneurysm from continuing to enlarge and ultimately rupture. Unfortunately, this technique suffers from the possibility that the aneurysm will continue to enlarge due to the pressure being exerted by the blood flow onto the coil placed into the opening of the aneurysm. Accordingly, there exists a continual desire to develop and provide a system or mechanism for occluding the flow of blood or reducing the pressure exerted onto the walls of vessel at the location of the aneurysm.

SUMMARY

In overcoming the enumerated drawbacks and other limitations of the related art, the present disclosure provides an aneurysm closure clip for treating an aneurysm in a body vessel of a patient. The closure clip generally comprises a self-expanding frame having a proximal side and a distal side. The frame is configured to move between a collapsed state in which the proximal and distal sides are compressed for delivery and an expanded state in which the frame expands to engage the body vessel. The distal side of the frame includes at least two winged elements. Each winged element is adapted to interact with the inner wall of body vessel in order to secure the closure clip proximate to the aneurysm. The proximal side of the frame includes a seal element and a guide bar. The seal element is adapted to form a barrier and separate the aneurysm from the rest of the body vessel, thereby, reducing the pressure exerted on the walls of the body vessel proximate to the aneurysm. The guide bar is configured to be in communication with a guide wire used during the delivery of the closure clip to the aneurysm in the body vessel.

According to one aspect of the present disclosure, the frame has a closed circumference and may be constructed of a single component or multiple components; wherein the component(s) are comprised of one selected from the group of stainless steel and a superelastic material. The frame may optionally include a surface treatment or coating of a therapeutic agent, as well as at least one barb to anchor the frame to the body vessel.

The seal element of the closure clip includes a material layer comprised of a bioremodelable material, such as an extracellular matrix (ECM). Optionally, at least one of the winged elements of the closure clip may further comprise a similar material layer.

According to another aspect of the present disclosure, a method for delivering the closure clip to a targeted location in a body vessel proximate to an aneurysm is provided. This method generally comprises introducing a delivery catheter having a proximal and distal end into the body vessel where the distal end is located proximate to the targeted location. A closure clip as described herein is then provided and inserted in its collapsed state into the proximal end of the delivery catheter. A guide wire is then inserted into the proximal end of the delivery catheter with the end of the guide wire being adapted to make reversible contact with the guide bar present on the proximal side of the closure clip. The guide wire is manipulated by the physician or operator to move the closure clip through the delivery catheter and to deliver it to the targeted location in the body vessel. Upon delivery of the closure clip to the targeted location, the clip is allowed to move from its collapsed state to an expanded state for engagement with the body vessel. Engagement with the body vessel occurs when the winged elements and seal element contacts the inner wall of the body vessel to form a barrier between the aneurysm and the rest of the body vessel.

According to yet another aspect of the present disclosure, a closure clip delivery system used by a physician to deliver a closure clip to a targeted location proximate to an aneurysm in the vasculature of a patient is provided. The closure clip delivery system comprises a delivery catheter having a proximal end and a distal end, a guide wire, and a detachable closure clip that is in communication with the guide wire. The closure clip delivery system is inserted into the vasculature of the patient and manipulated by the physician through the use of the guide wire during the delivery of the clip to the targeted location.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

FIG. 3A is a partial cross-sectional schematic of a body vessel in which the aneurysm closure clip of FIG. 2A is being delivered to an aneurysm;

FIG. 3B is another partial cross-sectional schematic of the body vessel of FIG. 3A in which the aneurysm closure clip is being placed into the opening of the aneurysm;

FIG. 3C is another partial cross-sectional schematic of the body vessel of FIG. 3B in which the aneurysm closure clip has been delivered and placed into the opening of the aneurysm;

FIG. 3D is another cross-sectional schematic of the body vessel of FIG. 3C in which the aneurysm closure clip has successfully sealed the opening of the aneurysm.

DETAILED DESCRIPTION

Figure 1B:
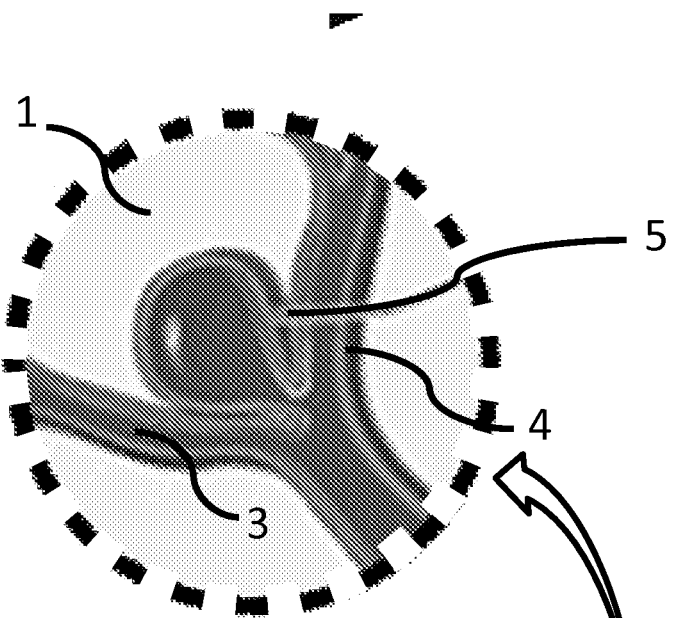
FIG. 1B is another perspective schematic magnifying the aneurysm shown in FIG. 1A.

The following description is merely exemplary in nature and is in no way intended to limit the present disclosure or its application or uses. The present disclosure specifically contemplates other embodiments not illustrated but intended to be included in the appended claims. It should be understood that throughout the description and drawings, corresponding reference numerals indicate like or corresponding parts and features.

The present disclosure generally provides an aneurysm closure clip having a self-expanding frame with a guide bar located on the proximal side of the frame and adapted to allow the frame to be retracted for delivery into a body vessel or vasculature of a patient. The aneurysm closure clip may optionally include a material layer that is circumferentially attached to the frame. The closure clip may be used by a physician to treat an aneurysm that has developed in the body vessel.

Figure 1A:
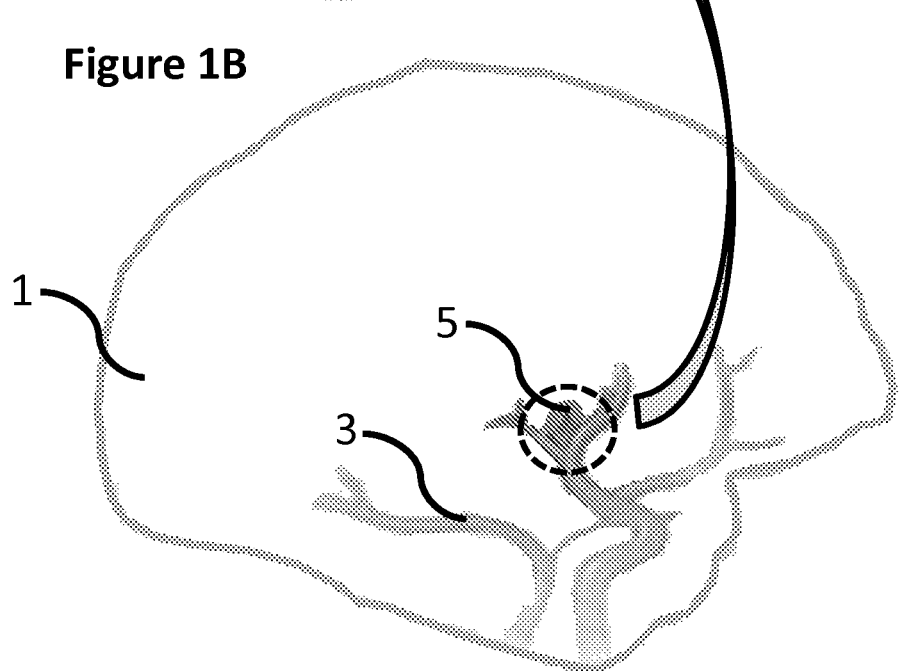
FIG. 1A is a perspective schematic of an aneurysm that can occur in a body vessel, such as an artery located in the brain.

Referring to FIGS. 1A and 1B, an aneurysm 5 is a localized, blood-filled bulge in the wall 4 of a blood or body vessel 3. Aneurysms 5 commonly occur, for example, in an artery at the base of the brain 1 or in the main artery carrying blood from the left ventricle of the heart, among others. When the size of an aneurysm 5 increases, there is a significant risk of rupture, resulting in severe hemorrhage or other complications, and even death. Aneurysms are generally classified by their macroscopic shape and can be described as being saccular in nature having a spherical shape and involving a portion of the vessel wall varying in size from about 5 to 20 cm in diameter.

Figures 2B, 2C:
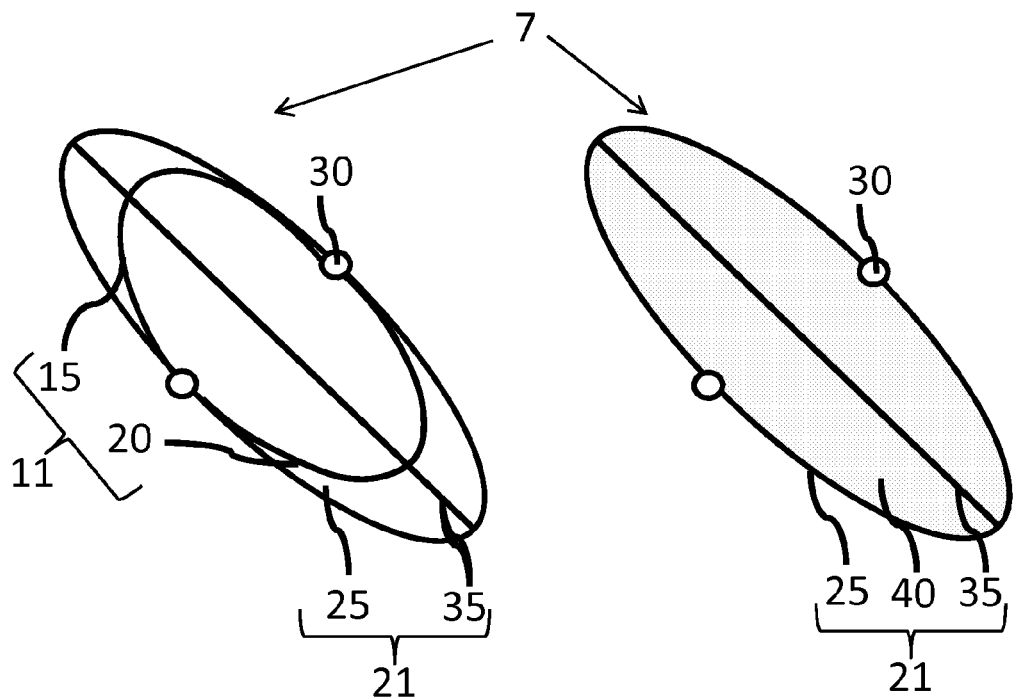
FIG. 2B is a perspective view of the distal side of the aneurysm closure clip of FIG. 2A.
FIG. 2C is a perspective view of the proximal side of the aneurysm closure clip of FIG. 2A.
Figure 2A:
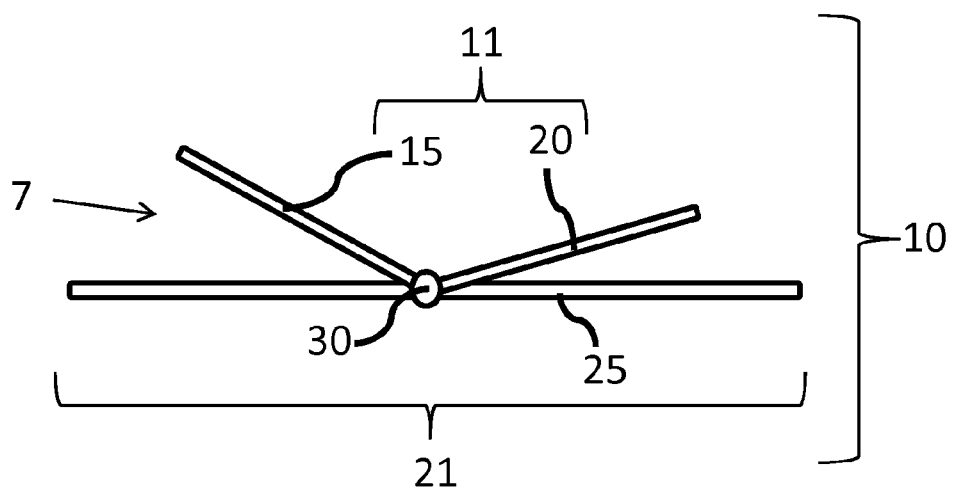
FIG. 2A is a perspective view of an aneurysm closure clip having a distal and proximal side prepared according to the teachings of the present disclosure.

Referring now to FIGS. 2A and 2B, the frame 10 of the aneurysm closure clip 7 prepared according to one aspect of the present disclosure comprises both a distal side 11 and a proximal side 21. The distal side 11 includes at least two winged elements 15, 20 coupled to a seal element 25 of the proximal side 21 through the use of a connector 30. The frame 10 is configured to move between a collapsed state in which the winged elements 15, 20 are compressed into near proximity with the seal element 25 for delivery and retrieval to the location of an aneurysm in the blood vessel or vasculature of a patient and an expanded state in which the frame 10 expands allowing the winged elements 15, 20 and the seal element 25 to engage the walls of the blood vessel at the site of the aneurysm.

Still referring to FIGS. 2A and 2B, the frame 10 is preferably made from a resilient material, such as a metal wire comprised of stainless steel or a superelastic material (e.g., Nitinol). Although a wire with a round surface is depicted in the figures, one skilled-in-the-art will understand that other types of wires, e.g., flat, square, or triangular, may be used to form the frame. One skilled in the art will further understand that the frame 10 could be made using a coil, a tube, or a solid bar without departing from scope of the disclosure. In one example, the frame 10 may be comprised of multiple wire strands with separate strands making up the winged elements 15, 20, the seal element 25 and the guide bar 35; each of the strands being coupled together through the use of a connector 30. The frame 10 may also be comprised of a single wire strand that makes up the winged elements 15, 20, the seal element 25, and guide bar 35 with the ends of the wire strand being attached together at the connector 30. In either case, the resulting frame 10 exhibits a closed circumference. A wire strand may be fabricated into the winged elements 15, 20, the seal element 25, and/or the guide bar 35 through the use of stamping or cutting from a sheet (e.g., by laser, etc.) or via various molding techniques or a similar method. Further finishing procedures can be performed after the frame 10 has been cut or formed, including, but not limited to, polishing, deburring, and adding surface treatments or coatings. Such surface treatments or coatings may include a therapeutic agent, such as antiproliferative agents, anti-inflammatory agents, and anti-platelet agents, among others.

According to another aspect of the present disclosure, the frame 7 may be made from a metal or metal alloy selected as one from the group of platinum, stainless steel, iridium, palladium, tungsten, gold, shape memory alloys, and combinations or mixtures thereof. In the case of shape memory alloys, such as Nitinol, the alloy is typically compressed or partially expanded when in its martensitic state and fully expanded in its austenitic state. During the construction of the frame 10, heating treating may be performed such that the winged elements 15, 20 and seal element 25 will be in the austenitic state when exposed to body temperature. Prior to insertion into the body, the aneurysm closure clip 7 may be maintained at a low temperature within the martensitic range in order to facilitate delivery. Upon delivery to a desired bodily location, the closure clip 7 may be warmed to at least the body temperature so that it can expand to the desired configuration.

The metal or metal alloy is selected to minimize or limit the potential for surface contamination and preferably is substantially free of any surface oxidation. Optionally, the connector 30, the frame 10, or a portion thereof may include a radiopaque or echogenic feature, including but not limited to a marker band, to assist in locating the aneurysm closure clip 7 proximate to the aneurysm in the vasculature through the use of x-ray fluoroscopy or sonography.

The connector 30 may be include a small piece of a metal cannula or tube with the ends of the frame inserted therein and secured with solder, a weld, adhesive, crimping, or the like. The ends of the frame may also be joined directly without a metal cannula through the use of soldering, welding, or any other method known to one skilled-in-the-art. At least one of the connectors 30 may be comprised of a simple 90 degree turn in the wire strand or a coil with approximately one and a quarter turns, among other types of bends. The use of a coil bend will produce superior bending fatigue characteristics than that of the simple bend when the frame 10 is made from stainless steel. On the other hand, when the frame 10 is formed from Nitinol (NiTi) or any other superelastic alloy, the use of a bend may actually be preferable. Other types of bends suitable for use as the connector 30 in the aneurysm closure clip 7 of the present disclosure is described in the intraluminal device of Pavcnik, et al. in U.S. Pat. No. 6,508,833, the entire contents of which are hereby incorporated by reference.

The winged elements 15, 20 may be made into various shapes, including but not limited to a half rounded bar, a semi-circle, or a semi-oval as shown in FIG. 2B. The shape of the winged elements 15, 20 are selected such that each element will exert an outward force on the inner wall of the blood vessel or vasculature that has developed into an aneurysm in order to assist the device in maintaining its location over the opening of the aneurysm.

Referring now to FIGS. 2B and 2C, the proximal side 21 of the closure clip 7 includes a seal element 25 and a guide bar 35. The guide bar 35 extends the length of the proximal side 21 and is used to manipulate the closure clip 7 during the delivery of the closure clip 7 to the aneurysm in the blood vessel. One skilled in the art will understand that the guide bar 35 may be located in other positions, such as extending the width of the proximal side 21 instead of the length of the proximal side 21 without exceeding the scope of the present disclosure.

The seal element 25 may be made into various shapes and sizes, including but not limited to a circle or an oval. The shape and size of the seal element 25 is selected such that the element will cover the opening of the aneurysm, thereby forming a seal or barrier between the aneurysm and the blood vessel or vasculature of the patient. The purpose of the seal element 25 is to seal off the aneurysm from the vessel, thereby, reducing or eliminating the pressure being exerted on the aneurysm. The seal element 25 is covered by a material layer 40 that will act as a barrier to seal the opening of aneurysm from the rest of the patient's vasculature.

Figures 2D, 2E:
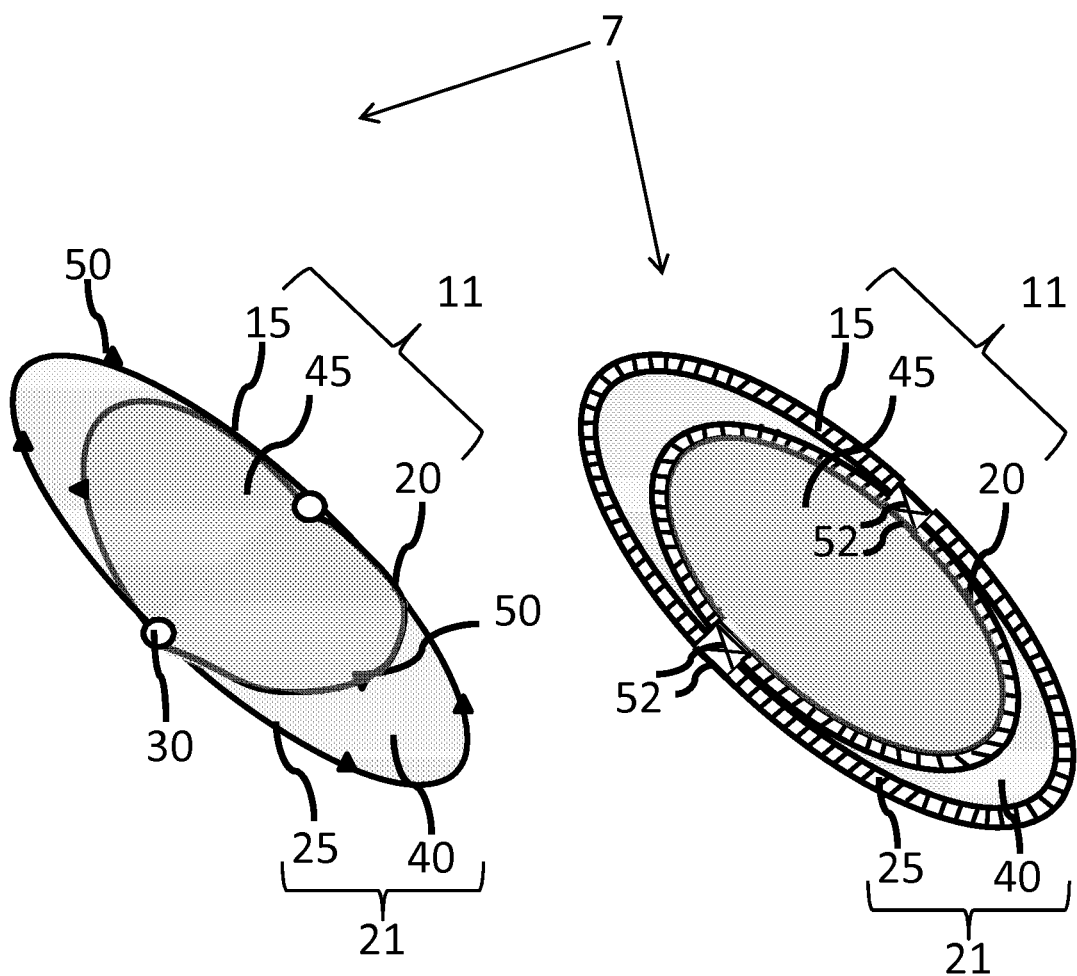
FIG. 2D is another perspective view of the distal side of an aneurysm closure clip prepared according to the teachings of the present disclosure.
FIG. 2E is another perspective view of the distal side of an aneurysm closure clip prepared according to the teachings of the present disclosure.

Referring now to FIG. 2D, according to another aspect of the present disclosure, the winged elements 15, 20 may optionally include a material layer 45 that can further assist in holding the closure clip 7 in place at the site of the aneurysm and to separate the aneurysm from the rest of the blood vessel. At least one of the winged elements 15, 20 and the seal element 25 may include one or more barbs 50 to anchor the closure clip 7 to the wall of a vessel following its deployment. The barb 50 may be any type of structure 4 attached to the frame 10 and so configured as to be able to anchor the clip 7 within the vessel. In order to facilitate anchoring, the structure of the barb 50 may comprise a bend, hook, or a sharp point for better penetration into the wall of the vessel.

Still referring to FIG. 2D, the material layers 40, 45 may comprise a connective tissue material, such as a bioremodelable material. In this aspect of the present disclosure, the bioremodelable material is used to temporarily adhere the frame 10 to the walls of a body vessel in which the closure clip 7 is deployed in order to form a seal between the aneurysm and the rest of the blood vessel or vasculature of the patient. As used herein, a bioremodelable material may include remodelable collagenous materials, whether reconstituted or naturally-derived, including, for example, collagenous materials isolated from a warm-blooded vertebrate, especially a mammal. Such isolated collagenous materials can be processed so as to have remodelable, angiogenic properties and to promote cellular invasion and ingrowth of adjacent tissues to generate a new, remodeled tissue structure.

Suitable bioremodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials may include but not be limited to intestinal submucosa, such as small intestinal submucosa, stomach submucosa, urinary bladder submucosa, and uterine submucosa. Additional information related to remodelable ECM materials useful in the present disclosure, as well as to their isolation and treatment can be in U.S. Pat. Nos. 4,902,508, 5,554,389, 5,993,844, 6,206,931, and 6,099,567, the contents of which are hereby incorporated by reference.

Remodelable ECM tissue materials harvested as intact sheets from a mammalian source and processed to remove cellular debris advantageously retain at least a portion of and potentially all of the native collagen microarchitecture of the source extracellular matrix. This matrix of collagen fibers provides a scaffold to facilitate and support tissue ingrowth, particularly in bioactive ECM implant materials, such as porcine small intestinal submucosa or SIS (Surgisis® Biodesign™, Cook Medical, Bloomington Ind.), that are processed to retain an effective level of growth factors and other bioactive constituents from the source tissue. In this regard, when the aneurysm closure clip of the present disclosure incorporates this sort of material, cells will invade the remodelable material upon implantation eventually leading to the generation of a newly-remodeled, functional tissue structure.

Submucosa-containing or other ECM tissue used in the invention is preferably highly purified, for example, as described in U.S. Pat. No. 6,206,931 to Cook et al, which is hereby incorporated by reference. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may exibit a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. One skilled in the art will understand that the submucosa or other ECM material used herein may exhibit properties that differ from the preferred amounts described above without exceeding the scope of the present disclosure.

In general, a submucosa or other ECM material may optionally retain one or more bioactive components that induce, directly or indirectly, a cellular response such as a change in cell morphology, proliferation, growth, protein or gene expression. Suitable bioactive agents may include but not be limited to one or more bioactive agents that are native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF), as well as other native bioactive agents, such as but not limited to proteins, glycoproteins, proteoglycans, and glycosaminoglycans. The ECM materials may include heparin, heparin sulfate, hyaluronic acid, fibronectin, cytokines, and the like.

Further, in addition or as an alternative to the inclusion of such native bioactive components, non-native bioactive components such as those synthetically produced by recombinant technology or other methods (e.g., genetic material such as DNA), may be optionally incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic), or during or after delivery of the aneurysm closure clip to a targeted site in the patient.

Referring now to FIG. 2E, according to another aspect of the present disclosure, the winged elements 15, 20 and seal element 25 of the frame 10 may comprise one or more coils (or tubular members) connected by one or more retention members or wires 52. For example, a single wire 52 may be run through the orifice of the coil or hollow tubular member of the seal element 25 one or more times, at which point the opposite ends of the wire are run toward each other through the coil of the seal element 25. The ends of the wire 52 may then be extended through the coils of winged elements 15, 20 toward opposite ends in each case, and looped back into the coil of the seal element 25, whereby the excess free ends can be clipped and crimped, tied, or further stabilized as necessary. In other words, the ends of the wires 52 interact with one another in such as manner that the coils form the seal element 25 and winged elements 15, 20. Additional examples, as well as other means of constructing and connecting the winged elements 15, 20 and seal element 25 of the present disclosure is described in the closure device of Pavcnik in co-pending U.S. patent application Ser. No. 12/813,489, filed Jun. 10, 2010, the entire contents of which are hereby incorporated by reference.

To facilitate the joining of one or more coils used in the construction of the frame 10, or to facilitate the joining of an portion of the frame 10 to a material layer described herein, any one of the various coiled structures may be partially stretched to create interrupted regions or open area grooves to facilitate linkage between coils and/or material layer using for example, wires or sutures. For example, coil grooves may facilitate linkages between the winged elements 15, 20 and seal element 25 of the frame 10 by providing open area connections to facilitate wire exchanges between the coil grooves. Coil grooves may also provide open area connections facilitating suture exchanges between the seal element and a material layer.

According to another aspect of the present disclosure, a closure clip delivery system is provided. Referring now to FIGS. 3A and 3B, the closure clip delivery system 8 comprises a delivery tube, such as a catheter 55 having a proximal 56 and a distal 57 end, a guide wire or push rod 60, and a closure clip 7. The closure clip delivery system 8 utilizes a delivery catheter 55 to establish a pathway through the vasculature 3 of the patient. The delivery catheter 55 is inserted into the vasculature 3 of the patient to a preselected or targeted location. More specifically, the distal end 57 of the catheter 55 in the closure clip delivery system 8 is positioned proximate to an aneurysm 5 or other abnormality in the vasculature 3. A closure clip 7 is placed into the proximal end 56 of the catheter 55 and pushed through the catheter 55 through the use of the guide wire 60 or push rod until the clip 7 exits the distal end 57 of the catheter 55. One end of the guide wire 60 is reversibly coupled to the guide bar 35 on the proximal side 21 of the closure clip 7 through the use of a hook or any other means known to one skilled in the art. The other end of the guide wire 60 may extend beyond the proximal end 56 of the catheter 55 in order to be accessible for manipulation by a physician or other attendant.

The delivery tube, i.e., the catheter 55, and/or the guide wire 60, may be made of any material known to one skilled-in-the-art, including but not limited to woven Dacron®, polyvinylchloride, polyurethane, polytetrafluoroethylene (PTFE), silicone, and nylon, as well as various metals and metal alloys, such as steel and Nitinol. The length and diameter of the delivery tube may be any size preselected for the intended delivery of the closure clip 7 to the aneurysm 5 in the vasculature 3 of the patient.

Referring now to FIG. 3C, once the closure clip 7 is delivered to the targeted location at the aneurysm 5 and the guide wire 60 becomes detached from the closure clip 7, the guide wire 60 may be removed along with the catheter 55. The winged elements 15, 20 make contact with the inner wall 4 of the blood vessel within the aneurysm 5, thereby, holding the closure clip 7 in position and allowing the seal element 25 to establish contact with the wall 4 of the blood vessel 3. Overtime, the growth of the aneurysm 5 is stopped because of the barrier 25 formed at the opening of the aneurysm 5 reduces or eliminates any pressure being exerted upon the aneurysm 5. The connective tissue of the blood vessel wall 4 interacts with the extracellular matrix material layer in the seal element 25 as shown in FIG. 3D to form a connective tissue structure 65.

Figure 4:
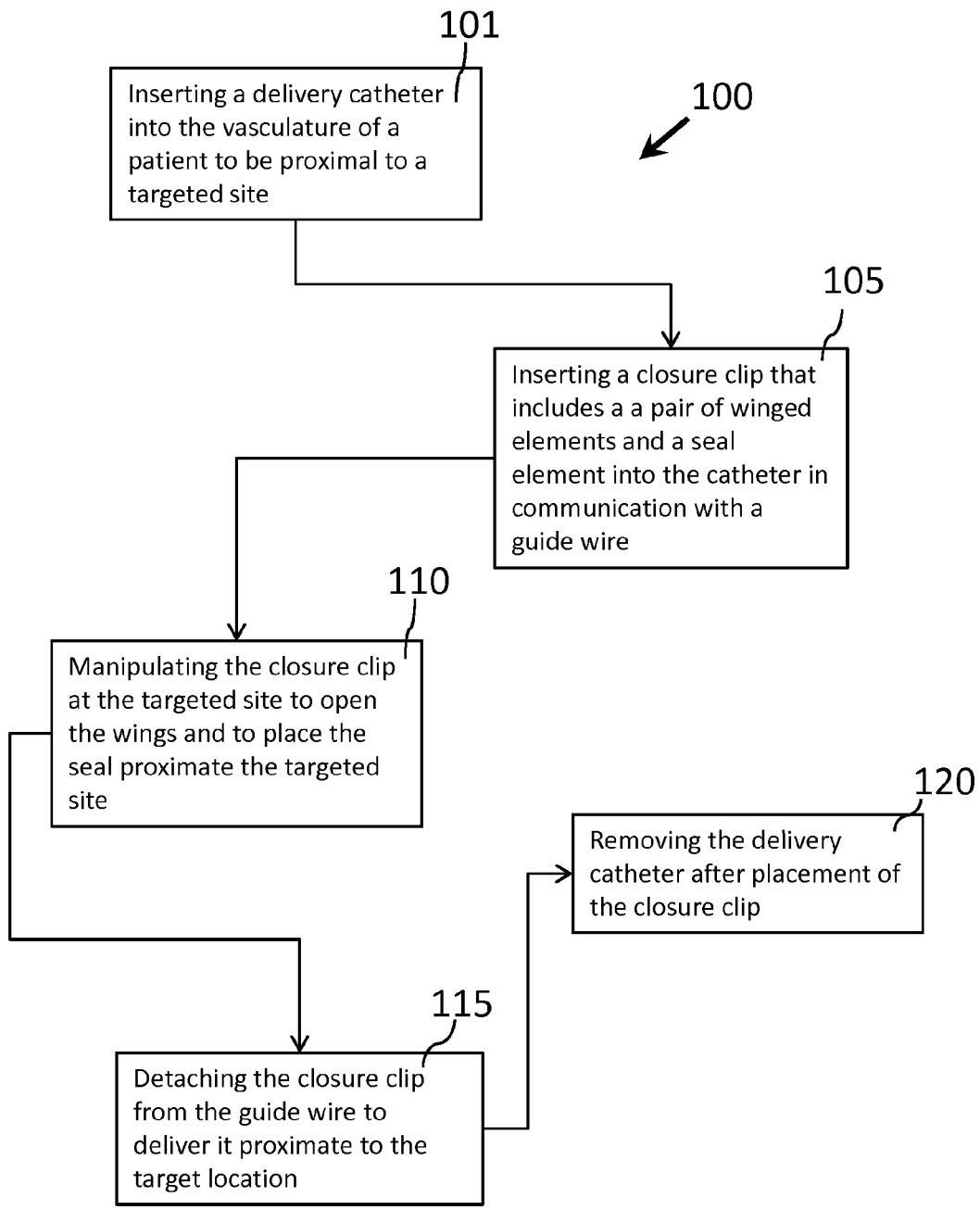
FIG. 4 is a flowchart describing a method of delivering an aneurysm closure clip into the body vessel of a patient according to one aspect of the present disclosure.

Referring now to FIG. 4, it is another objective of the present disclosure to provide a method 100 of delivering a closure clip to an aneurysm present in the vasculature of a patient. The method 100 comprises the steps of inserting a delivery catheter into the vasculature of a patient to be proximal to a pre-selected targeted site; inserting 105 a closure clip as previously described herein into the delivery catheter; manipulating 110 the closure clip in a predetermined manner through the use of a guide wire in order to open the winged elements and to place the seal element proximate to the targeted site; and detaching 115 the closure clip from the guide wire to deliver it proximate to the desired or targeted location. The delivery catheter and guide wire can be removed 120 after the closure clip is delivered.

This method 100 uses the closure clip delivery system 8 as previously described in the present disclosure. More specifically, the closure clip delivery system 8 comprises a delivery tube, such as a catheter 55, guide wire 60, and a closure clip 7. The closure clip 7 includes a proximal side 21 having a seal element 25 and a guide bar 35. The guide bar 35 may be reversibly coupled to the guide wire 60 in order for the physician to manipulate the closure clip 7 during delivery to ensure that the seal element 25 forms a barrier between the aneurysm 5 and the rest of the blood vessel 3.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An aneurysm closure clip for treating an aneurysm in a body vessel of a patient, the closure clip comprising:
    a self-expanding frame having a proximal side and a distal side with respect to a delivery position in a target location, in which the proximal side is disposed inside a blood vessel and the distal side is disposed in an aneurism formed in a wall of the blood vessel; the frame configured to move between a collapsed state in which the proximal and distal sides are compressed for delivery and an expanded state in which the frame expands to engage the blood vessel;
    wherein the distal side includes at least two winged elements; each winged element configured to be inserted into the aneurism and adapted to interact with the inner wall of the body vessel in order to secure the closure clip proximate to the aneurysm;
    wherein the proximal side includes a seal element and a guide bar; the seal element adapted to separate the aneurysm from the rest of the body vessel and to reduce the pressure exerted on the walls of the body vessel proximate to the aneurysm; the guide bar configured to be in communication with a guide wire during delivery of the closure clip to the aneurysm;
    a connector, retention member, or wire, forming two connector points on laterally opposite sides of the seal element,
    wherein in each of the two connector points, the seal element and the at least two winged elements are all joined together, and
    wherein the at least two winged elements and the seal element are all separate from one another outside of the connector points.

2. The closure clip of claim 1, wherein the frame is comprised of one selected from the group of stainless steel and a superelastic material.

3. The closure clip of claim 1, wherein the frame has a closed circumference.

4. The closure clip of claim 3, wherein the frame is constructed of at least one coil with one or more wires run through the orifice of coil;
    wherein the ends of the wires interact with one another such that the coils form the winged elements and seal element.

5. The closure clip of claim 1, wherein the frame includes a surface treatment or coating of a therapeutic agent.

6. The closure clip of claim 1, wherein the seal element includes a material layer comprising an extracellular matrix (ECM).

7. The closure clip of claim 6, wherein the extracellular matrix is comprised of small intestinal submucosa (SIS).

8. The closure clip of claim 1, wherein at least one of the winged elements further comprises a material layer; the material layer being an extracellular matrix (ECM).

9. The closure clip of claim 8, wherein the extracellular matrix is comprised of small intestinal submucosa (SIS).

10. The closure clip of claim 1, wherein the frame further comprises at least one selected from the group of one or more barbs to anchor the frame to the body vessel and a radiopaque or echogenic marker band to assist in locating the closure clip in the body vessel.

11. A method for delivering a closure clip to a targeted location in a body vessel proximate to an aneurysm; the method comprising the steps of:
    introducing a delivery catheter having a proximal and distal end into the body vessel; the distal end being located proximate to the targeted location in the body vessel;
    providing a closure clip; the closure clip comprising:
        a self-expanding frame having a proximal side and a distal side with respect to a delivery position in a target location, in which the proximal side is disposed inside a blood vessel and the distal side is disposed in an aneurysm formed in a wall of the blood vessel; the frame configured to move between a collapsed state in which the proximal and distal sides are compressed for delivery and an expanded state in which the frame expands to engage the blood vessel;
        the distal side including at least two winged elements; each winged element configured to be inserted into the aneurism and adapted to interact with the inner wall of the body vessel in order to secure the closure clip proximate to the aneurysm; and
        the proximal side including a seal element and a guide bar; the seal element adapted to separate the aneurysm from the rest of the body vessel and to reduce the pressure exerted on the walls of the body vessel proximate to the aneurysm; the guide bar configured to be in communication with a guide wire during delivery of the closure clip to the aneurysm in the body vessel;
    wherein the seal element and the at least two winged elements are all joined together by a connector, retention member, or wire forming two connector points on laterally opposite sides of the seal element,
        wherein in each of the two connector points, the seal element and the at least two winged elements are all joined together,
    inserting the closure clip in the collapsed state into the proximal end of the delivery catheter;
    inserting an end of a guide wire into the proximal end of the delivery catheter; the end of the guide wire adapted to make reversible contact with the guide bar; the guide wire adapted to move the closure clip through the delivery catheter;
    delivering the closure clip to the targeted location in the body vessel; and
    allowing the closure clip to move to the expanded state for engagement with the body vessel.

12. The method of claim 11, wherein the step of allowing the closure clip to move to the expanded state for engagement with the body vessel includes the winged elements and seal elements contacting the inner wall of the body vessel in order to form a barrier between the aneurysm and the rest of the body vessel.

13. A closure clip delivery system used by a physician to deliver a closure clip to a targeted location proximate to an aneurysm in the vasculature of a patient; the closure clip delivery system comprising:

a delivery catheter having a proximal end and a distal end, the catheter inserted into the vasculature of the patient;

a guide wire through which the physician can manipulate the closure clip during delivery of the clip to the targeted location; and a detachable closure clip, the closure clip comprising:
  a self-expanding frame having a proximal side and a distal side with respect to a delivery position in a target location, in which the proximal side is disposed inside a blood vessel and the distal side is disposed in an aneurism formed in a wall of the blood vessel; the frame configured to move between a collapsed state in which the proximal and distal sides are compressed for delivery and an expanded state in which the frame expands to engage the blood vessel;
  the distal side including at least two winged elements; each winged element configured to be inserted into the aneurism and adapted to interact with the inner wall of the body vessel in order to secure the closure clip proximate to the aneurysm; and
  the proximal side including a seal element and a guide bar; the seal element adapted to separate the aneurysm from the rest of the body vessel and to reduce the pressure exerted on the walls of the body vessel proximate to the aneurysm; the guide bar configured to be in communication with a guide wire during delivery of the closure clip to the aneurysm in the body vessel,
a connector, retention member, or wire, forming two connector points on laterally opposite sides of the seal element,
wherein in each of the two connector points, the seal element and the at least two winged elements are all joined together, and
wherein the at least two winged elements and the seal element are all separate from one another outside of the connector points.

14. The closure clip delivery system of claim 13, wherein at least one of the winged elements and the seal element includes a material layer comprised of bioremodelable material.

15. The closure clip delivery system of claim 14, wherein the bioremodelable material is comprised of an extracellular matrix material (ECM).

* * * * *